(12) United States Patent
Maes

(10) Patent No.: US 10,154,211 B2
(45) Date of Patent: Dec. 11, 2018

(54) CIRCUIT CONTROLLER FOR CONTROLLING A PIXEL CIRCUIT AND A METHOD OF CONTROLLING A PIXEL CIRCUIT

(71) Applicant: TELEDYNE DALSA B.V., Eindhoven (NL)

(72) Inventor: Willem Hendrik Maes, Lommel (BE)

(73) Assignee: TELEDYNE DALSA B.V., Eindhoven (NL)

( * ) Notice: Subject to any disclaimer, the term of this patent is extended or adjusted under 35 U.S.C. 154(b) by 51 days.

(21) Appl. No.: 15/513,113

(22) PCT Filed: Nov. 20, 2014

(86) PCT No.: PCT/EP2014/075143
§ 371 (c)(1),
(2) Date: Mar. 21, 2017

(87) PCT Pub. No.: WO2016/078713
PCT Pub. Date: May 26, 2016

(65) Prior Publication Data
US 2017/0264838 A1 Sep. 14, 2017

(51) Int. Cl.
*H04N 5/335* (2011.01)
*H04N 5/355* (2011.01)
(Continued)

(52) U.S. Cl.
CPC ......... *H04N 5/3559* (2013.01); *A61B 6/4208* (2013.01); *H04N 5/3575* (2013.01);
(Continued)

(58) Field of Classification Search
CPC ............ H04N 5/3559; H04N 5/35536; H04N 5/3575; H04N 5/37452; H04N 5/374; H04N 5/378
(Continued)

(56) References Cited

U.S. PATENT DOCUMENTS 6,608,575 B2 *  8/2003  Bazarjani .............. H03M 3/496
                                                    341/143
8,786,745 B2 *  7/2014  Kawahito .......... H04N 5/35581
                                                    250/208.1
(Continued)

FOREIGN PATENT DOCUMENTS

WO      99/44359     9/1999
WO      99/62244    12/1999
(Continued)

OTHER PUBLICATIONS

International Search Report dated May 6, 2015 issued in related co-pending PCT/EP2014/075143.

*Primary Examiner* — Ngoc-Yen Vu
(74) *Attorney, Agent, or Firm* — McGuireWoods LLP

(57) ABSTRACT

A pixel circuit comprises a first capacitor, a photo diode and a switch. A voltage source generates a reference voltage to reset the pixel circuit. The pixel circuit is reset for a first reset time period by electrically coupling a cathode of the photo diode and a first capacitor terminal to the voltage source. The cathode is decoupled from the voltage source and the photo diode is exposed to light for an accumulation time period. After the accumulation time period, a first reference voltage is sampled. The cathode is then coupled, via the switch, to the first capacitor terminal for a selected transfer time period, during which a second signal voltage is sampled. After the selected transfer time period, a first signal voltage is sampled with the cathode decoupled. The pixel circuit is then reset for a second reset time period, after which a second reference voltage value is sampled.

11 Claims, 4 Drawing Sheets

(51) Int. Cl.
*H04N 5/357* (2011.01)
*H04N 5/3745* (2011.01)
*A61B 6/00* (2006.01)
*H04N 5/374* (2011.01)
*H04N 5/378* (2011.01)
*H04N 5/217* (2011.01)
*H04N 5/363* (2011.01)

(52) U.S. Cl.
CPC ......... *H04N 5/35536* (2013.01); *H04N 5/374* (2013.01); *H04N 5/378* (2013.01); *H04N 5/37452* (2013.01); *H04N 5/363* (2013.01)

(58) Field of Classification Search
USPC ................................. 348/294, 308–310, 241
See application file for complete search history.

(56) References Cited

U.S. PATENT DOCUMENTS

| | | | |
|---|---|---|---|
| 9,686,483 B2* | 6/2017 | Bagwell | H04N 5/33 |
| 9,762,824 B2* | 9/2017 | Boemler | H04N 5/3575 |
| 9,774,811 B1* | 9/2017 | Ebihara | H03K 4/502 |
| 9,924,121 B2* | 3/2018 | Onishi | H04N 5/3559 |
| 2010/0271517 A1 | 10/2010 | De Wit et al. | |
| 2011/0194007 A1* | 8/2011 | Kim | H04N 5/3575 |
| | | | 348/308 |

FOREIGN PATENT DOCUMENTS

| | | |
|---|---|---|
| WO | 2008/11550 A2 | 9/2008 |
| WO | 2009/156927 A2 | 12/2009 |
| WO | 2014/008946 A1 | 1/2014 |

\* cited by examiner

CIRCUIT CONTROLLER FOR CONTROLLING A PIXEL CIRCUIT AND A METHOD OF CONTROLLING A PIXEL CIRCUIT

CROSS-REFERENCE TO RELATED APPLICATIONS

This application is the national stage application of and claims priority to International Patent Application No. PCT/EP2014/075143 filed on Nov. 20, 2014, the disclosure of which is incorporated by reference herein in its entirety.

FIELD OF THE INVENTION

The invention relates to a circuit controller for controlling a pixel circuit, a pixel circuit, an image sensor, a radiation detector and a method of controlling a pixel circuit.

BACKGROUND ART

Image sensors are widely used in digital still cameras, security cameras, medical, automobiles, and other applications. Image sensors may work on the basis of pixel circuits. The pixel circuit usually comprises a photo diode and a plurality of transistors. The photo diode collects charges during exposition to light. The plurality of transistors transfers the charges to a bank of capacitors in which the charges are stored as voltages across the capacitors. The voltages are then read by suitable readout circuitry and processed to generate an output image.

Transferring of the charges to the bank of capacitors can be performed in various ways.

For example, a transfer switch electrically coupled to the cathode of the photo diode may be used to transfer the charges to a capacitive conversion node in the pixel circuit. The charges are stored in the capacitive conversion node. A pixel voltage may be sampled by a sampling circuit and referred to the bank of capacitors for subsequent readout.

In order to properly transfer the charges between the photo diode and the capacitive conversion node after exposure, the photo diode needs to be depleted of charges before exposure. This can be accomplished by resetting the photo diode so that the photo diode is depleted of charges before exposure. A common way to reset the photo diode is to electrically couple the cathode of the photo diode to a reference voltage via a reset switch. The reference voltage contributes to a reverse biasing of the photo diode. Depletion of the photo diode is enhanced with increased reference voltage. However, resetting the photo diode and capacitance, contributes to increased reset noise. Correlated double sampling (CDS) can be used to virtually eliminate the reset noise. After exposure of the photo diode, the capacitive conversion node is reset to its initial value, while the signal voltage is still stored in the photo diode. A reference voltage value is readout after exposure. Immediately after the reference voltage value is read out, the charges stored in the photo diode are transferred via the switch to the capacitive conversion node. After transferring the charges, a corresponding signal voltage value is readout. Thus the two readout values are said to be correlated. A difference between the two readout values represents the actual light induced voltage change. Since the two readout values are correlated, the reset noise, i.e. the noise contribution given by the reset operation substantially disappears.

In the example of the pixel circuit described above, the capacitive conversion node has typically a limited storage capacity which limits the use of the pixel circuit to a light intensity corresponding to the limited storage capacity of the capacitive conversion node. Higher light intensity will result in saturation of the capacitive conversion node and reduced dynamic range.

A number of solutions have been sought to obtain an extended dynamic range in a pixel circuit. For example, US patent application US2006/0071147A1 discloses a pixel circuit that operates in two different modes based on the light intensity level impinging on the photo diode. Under high light intensities, the capacitive conversion node is increased by turning-on the transfer switch during the readout operation. Alternatively, under low light intensities, the pixel circuit may operate with the transfer gate turned-off. However, the light intensity level is monitored before operating the pixel circuit in the two different modes. Further, since sampling occurs at different light conditions, systematic errors can be introduced in the sampling. Eventually, the systematic errors need to be calibrated out in a signal post-processing stage. In order to operate the pixel circuit disclosed in US2006/0071147A1, a cumbersome control of the pixel circuit is thereby required. There is a need for a simpler control of the pixel circuit.

SUMMARY OF THE INVENTION

One of the objects of the invention is to simplify the control of a pixel circuit while at the same time providing a high dynamic range for reading out the pixel circuit.

According to the invention this object is achieved by a circuit controller as described in claim 1. The circuit controller controls a pixel circuit comprising a first switch, a second switch, a first capacitor, a photo diode for accumulating charge carriers upon exposure to incident light, and a sampling circuit for sampling a voltage value at a first capacitor terminal. The first switch electrically couples, when switched on a first capacitor terminal to a voltage source. The second switch electrically couples, when switched-on, the first capacitor terminal to a cathode of the photo-diode.

The circuit controller is configured to sample a first reference voltage value and a first signal voltage value. The pixel circuit is initially reset for a first reset time period. After the first reset time period has passed, the photo diode is exposed to light for an accumulation time period. The first reference voltage value is sampled after the accumulation time period has passed. The first signal voltage value is sampled after transferring charges accumulated in a photo diode during light exposure, i.e. after the second switch has been switched-on for a selected transfer time period. Correlated doubled sampling is obtained by sampling the first reference voltage value and the first signal voltage value with no reset of the pixel circuit occurring between the two samplings. A first difference between the first signal voltage value and the reference voltage value may be used to indicate an amount of charge carriers accumulated in the photo diode during the accumulation time period.

The claimed circuit controller adds a second doubled sampling to the above correlated doubled sampling.

A second signal voltage value is sampled during the selected transfer time period. After the selected transfer time period has passed and the first signal voltage value has been sampled, a second pixel reset has been added. The first switch and the second switch are again switched-on for a second reset time period. After the second reset time period has passed, the first switch is switched-off. The second reference voltage value is sampled while the first switch is off and the second switch is on. The second doubled sampling is obtained by sampling the second reference voltage value and the second signal voltage value with a reset occurring between the two samplings.

The circuit controller described above uses a same single exposure of the photo diode for both the correlated doubled sampling and the second doubled sampling. After the same single exposure, the first reference voltage value, the second signal voltage value, the first signal voltage value and the second reference voltage value are sampled in a fixed sampling sequence as described above. During the selected transfer time period, the charge carries accumulated in the photo diode are redistributed among the first capacitor and a capacitance of the second switch (e.g. a gate oxide capacitance in the case of a Metal Oxide Semiconductor switch), thereby increasing the capacitance at the first capacitor terminal. For high light intensity, a second voltage difference between the second signal voltage value and the second reference voltage value may be used to indicate an amount of charge carriers accumulated in the photo diode during the accumulation time period.

For the same single exposure, the correlated double sampling may be used for reading out the pixel circuit for relatively low light intensity, while the second double sampling may be used for reading out the pixel circuit for relatively high light intensity. Thus the circuit controller provides a simpler way of reading out the pixel circuit on a same charge packet, thereby allowing for a high dynamic range. The claimed circuit controller may be e.g. used in radiological instruments for medical X-ray imaging wherein a patient's excessive exposure to X-ray radiation is avoided.

A further advantage provided by the claimed circuit controller is that the second reference voltage value and the second signal voltage value are sampled when the first switch and the second switch are controlled in the same state. Systematic errors due to the contribution of the process spread on the reset value, i.e. the so-called fixed pattern noise, are substantially cancelled-out.

The present invention further provides a pixel circuit, an image sensor, a radiation detector and a method of controlling a pixel circuit as described in the accompanying claims.

These and other aspects of the invention will be apparent from and elucidated with reference to the embodiment described hereinafter.

BRIEF DESCRIPTION OF THE DRAWINGS

These and other aspects of the invention are apparent from and will be elucidated with reference to the embodiments described hereinafter. In the drawings, FIG. 1 schematically shows an example of a pixel circuit and a circuit controller for controlling the pixel circuit.

It should be noted that items which have the same reference numbers in different Figures, have the same structural features and the same functions, or are the same signals. Where the function and/or structure of such an item has been explained, there is no necessity for repeated explanation thereof in the detailed description.

DETAILED DESCRIPTION OF EMBODIMENTS

Hereinafter for describing the Figures, if not otherwise stated, the following conventions are used: black dots indicate electrical nodes or electrical terminals, continuous lines connecting two points in a circuit indicate a direct electrical connection, dashed lines connecting two black dots in a circuit indicate an electrical coupling between the two nodes or terminals, i.e. one or more components may be used between the two points to electrically connect the two points.

Figure 1:
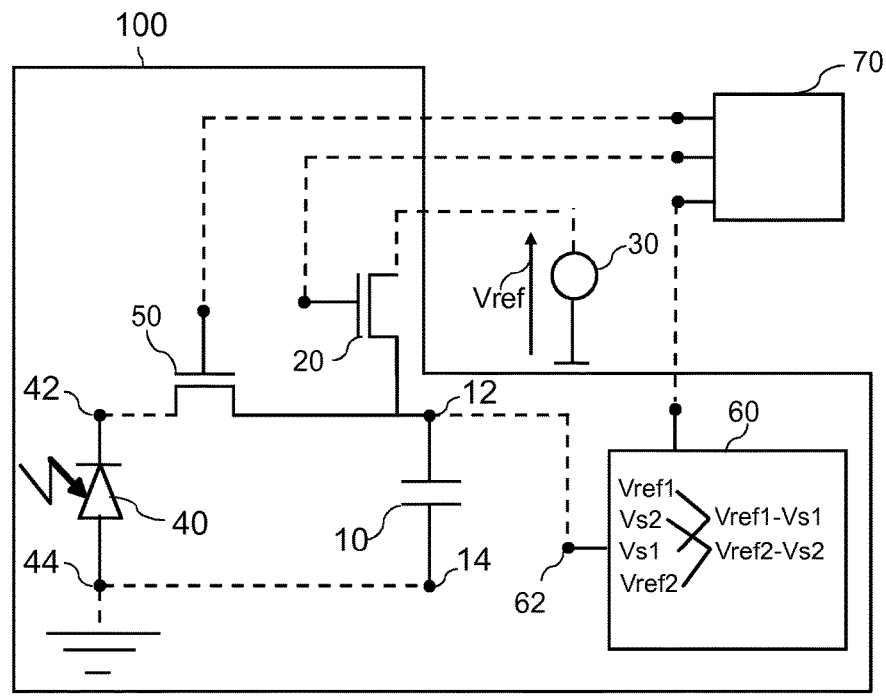

FIG. 1 schematically shows an example of a pixel circuit 100 and a circuit controller 70 for controlling the pixel circuit 100.

The pixel circuit 100 comprises a first capacitor 10, a first switch 20, a photo diode 40, a second switch 50, and a sampling circuit 60.

The first capacitor 10 has a first capacitor terminal 12 and a second capacitor terminal 14. The first capacitor 10 may be a diffusion capacitance, e.g. a n-type diffusion semiconductor region on a p-type semiconductor substrate. Alternatively, the diffusion capacitance may be implemented as p-type diffusion semiconductor region on a n-type semiconductor substrate. The diffusion capacitance may be isolated by the first switch 20 and the second switch 50 such that the diffusion is floating when e.g. the first switch 20 and the second switch 50 are switched off.

The photo diode 40 has a cathode 42 and an anode 44. The photo diode 40 may be a buried photo diode, for example an n-type semiconductor region buried on a p-type substrate. Alternatively, the photo diode 40 may be fabricated as p-type semiconductor region buried on a n-type substrate. The dashed line between the cathode 42 and a terminal of the second switch 50 indicates that there may not be a direct physical electrical connection between the cathode 42 and said terminal. Since the photo diode 40 may have a structure physically larger than the diffusion capacitance, a capacitance of the photo diode 40 may be substantially larger than the diffusion capacitance.

The first switch 20 electrically couples, when switched-on, the first capacitor terminal 12 to a voltage source 30. The voltage source 30 generates a reference voltage Vref. The photo diode 40 accumulates charge carriers upon exposure to incident light. The anode 44 is electrically coupled to the second capacitor terminal 14.

The second switch 50 electrically couples, when switched-on, the cathode 42 to the first capacitor terminal 12.

The first switch 20 and the second switch 50 are schematically drawn in the Figures as metal-oxide-semiconductor transistors (MOS transistors). However, the first switch 20 and the second switch 50 may be implemented in manner suitable for the specific implementation.

For example, the first switch 20 and the second switch 50 may comprise a transistor of the group of transistors consisting of: complementary metal oxide transistors, junction field effect transistors, metal effect semiconductor transistors, bipolar transistors, hetero-junction bipolar transistors, insulated-gate bipolar junction transistors or a combination thereof. The second switch 50 has always an inherent transfer capacitance, e.g. a transfer gate capacitance in case of a MOS transistor, which is arranged in parallel to the first capacitor 10.

The sampling circuit 60 has an input 62 electrically coupled to the first capacitor terminal 12 for sampling a voltage value at the first capacitor terminal 12.

The circuit controller 70 is configured to switch-on the first switch 20 and the second switch 50 for a first reset time period. After the first reset time period has passed, the circuit controller 70 switches off the second switch 50 such that the cathode 42 is electrically decoupled from the voltage source 30. During an accumulation time period, the photo diode 40 is exposed to light. In the accumulation time period the second switch 50 is off. Charge carriers are accumulated in the photo diode 40 during the accumulation time period. During the accumulation time period, the first switch 20 is switched off for electrically decoupling the first capacitor terminal 12 from the voltage source 30. After the first switch 20 is switched off, the sampling circuit 60 is controlled to sample a first reference voltage value Vref1.

After the accumulation time period, the circuit controller 70 switches on for a selected transfer time period the second switch 50 for transferring the charge carriers to the first capacitor 10.

After transferring the charge carriers, i.e. after the selected transfer time period has passed, the circuit controller 70 switches off the second switch 50 and controls the sampling circuit 60 to sample a first signal voltage value Vs1 at the first capacitor terminal 12.

During the selected transfer time period, the circuit controller 70 further controls the sampling circuit 60 to sample a second signal voltage value Vs2. The second signal voltage value Vs2 is sampled when the second switch 50 is switched on.

After sampling the first signal voltage value Vs1, the circuit controller 70 switches on the first switch 20 and the second switch 50 for a second reset time period. After the second reset time period has passed, the circuit controller 70 switches off the first switch 20, and controls the sampling circuit 60 to sample a second reference voltage value Vref2 when the first switch 20 is switched off and the second switched 50 is switched on.

By sampling the second signal voltage value Vs2 during the selected transfer time period, the charge storage capacity at the first capacitor terminal 12 is increased. When the second switch 50 is switched on, the first capacitor 10 is effectively arranged in parallel with a transfer capacitance of the second switch 50, thereby increasing the capacitance at the first capacitor terminal 12.

For example, the second switch 50 may be a metal oxide semiconductor (MOS) switch and the transfer capacitance may be a transfer gate capacitance arranged in parallel with the first capacitor 10.

During exposure, when the intensity level of the light impinging on the photo diode 40 causes the first capacitor 10 to saturate, the transfer capacitance can be used as an extra storage capacity to increase the dynamic range. When the second signal voltage value Vs2 is sampled, i.e. when the second switch 50 is on, the charge carriers are pulled out from photo diode 40 and transferred to the first capacitor 10 and the transfer capacitance. When the first signal voltage value Vs1 is sampled, i.e. when the second switch 50 is off, the charge carriers are located in the first capacitor 10. Sampling the second signal voltage value Vs2 at a selected portion of the selected transfer time period, will provide a pixel circuit reading with a higher dynamic range.

After sampling the first signal voltage value Vs1, the circuit controller 70 resets the pixel circuit 100 for a second reset time period. After the second reset time period has passed, the circuit controller 70 controls the sampling circuit 60 to sample the second reference voltage value Vref2. The second reference voltage value Vref2 corresponds to the second signal voltage value Vs2.

A same single exposure is performed on the pixel circuit 100, after which the first reference voltage value Vref1, the second signal voltage value Vs2, the first signal voltage value Vs1 and the second reference voltage value Vref2 are sampled in a fixed sampling sequence as described above. Thus the circuit controller 70 provides a simpler way of reading out the pixel circuit on a same charge packet, thereby allowing for a high dynamic range.

The first switch 20 and the second switch 50 are controlled in the same state during sampling of the second signal voltage value Vs2 and the second reference voltage value Vref2. The second reference voltage value Vref2 may be used as reference value for the sampling of the second signal voltage value Vs2. Since the second reference voltage value Vref2 and the second signal voltage value Vs2 are sampled when the first switch 20 and the second switch 50 are controlled in the same state, systematic errors due to the contribution of the process spread on the reset value are substantially cancelled-out. For example, the reset value in an image sensor may spread from one pixel circuit to another pixel due to circuit variation in the manufacturing process of the first capacitor 10, the first switch 20, the second switch 50 and interconnects between them, the circuit controller 70 and the sampling circuit 60. Those systematic variations, sometimes referred as to fixed pattern noise (FPN) may be cancelled out by referring the second signal voltage value Vs2 to the second reference voltage value Vref2 as described above.

Further, the circuit controller 70 controls the sampling circuit 60 to sample the voltages at the first capacitor terminal 12 during a repetitive period of time starting with the first reset time period and ending after sampling the second reference voltage value Vref2. The repetitive period of time may be used to read-out sequentially all pixel circuits in an image sensor.

The sampling circuit 60 may be implemented in any manner suitable for the specific implementation.

Figure 2:
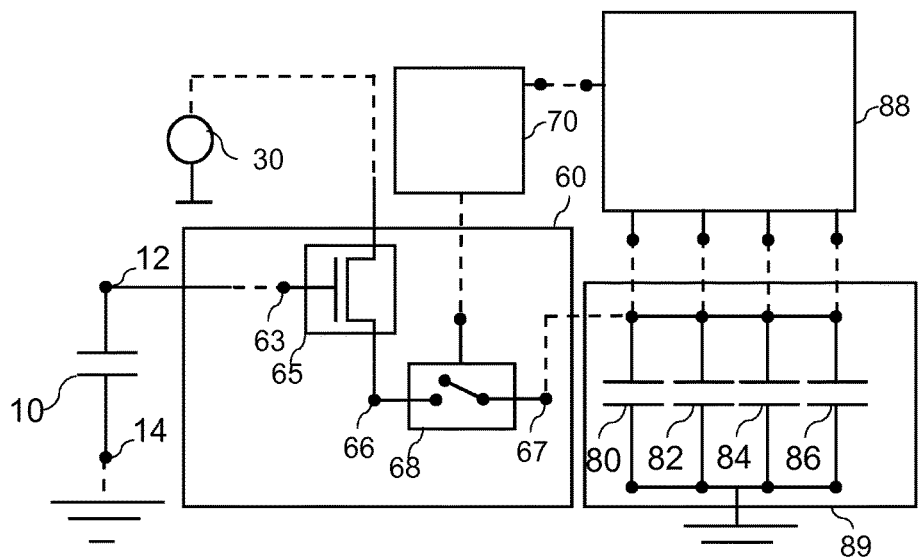
FIG. 2 shows an example of a sampling circuit.

For example, referring to FIG. 2, the sampling circuit 60 may comprise a buffer circuit 65 and a third switch 68. The buffer circuit 65 has an input 63 electrically coupled to the first capacitor terminal 12 and an output electrically connected to an input terminal 66 of the third switch 68. The buffer circuit 65 may be implemented in any manner suitable for the specific implementation. In FIG. 2, the buffer circuit 65 shown is a MOS source follower. However, the buffer circuit 65 may comprise one or more MOS transistors or other type of transistors for buffering the voltage at the first capacitor terminal 12.

An output 67 of the third switch 68 may be connected to a parallel array 89 of at least four capacitors 80, 82, 84 and 86 for storing the first reference voltage value Vref1, the second signal voltage value Vs2, the first signal voltage value Vs1 and the second reference voltage value Vref2, respectively. The output 67 may be coupled to the respective capacitor 80, 82, 84 or 86 via additional switches (not shown in FIG. 2), to for example select the desired capacitor value for storing the respective sampled voltage value. The third switch 68 may be controlled by the circuit controller 70 to control an array of pixel circuits arranged e.g. in a row or a column of an image sensor.

The parallel array 89 of at least four capacitors 80, 82, 84, 86 is electrically coupled to a readout circuitry 88 for reading the first reference voltage value Vref1, the second signal voltage value Vs2, the first signal voltage value Vs1 and the second reference voltage value Vref2.

The readout circuitry 88 may be implemented in any manner suitable for the specific implementation.

For example, the read out circuitry may be implemented with operational amplifiers and/or measurement circuits capable to measure the voltage values across the respective capacitors 82, 84, 86 and 88.

For example, the circuit controller 70 may control the read out circuitry and/or the readout circuitry 88 for determining a first voltage difference by subtracting the first signal voltage value Vs1 from the first reference voltage value Vref1 and a second voltage difference by subtracting the second signal voltage value Vs2 from the second reference voltage value Vref2. The first voltage difference may be used as a measure of the light impinging on the photo diode for low level of light intensity. The second voltage difference may be used as a measure of the light impinging on the photo diode for high level of light intensity.

For example, the circuit controller 70 may be configured for controlling the sampling circuit 60 to select the first voltage difference as an output voltage of the pixel circuit when the first voltage difference is smaller than a predetermined voltage value or the second voltage difference when the first voltage difference is larger the predetermined voltage value. The predetermined voltage value may correspond to a saturation level of the first capacitor 10, i.e. to a maximum level of discharge of the first capacitor 10.

The solution proposed will further described with reference to FIGS. 3 and 4 and the circuit of FIG. 1.

Figure 3:
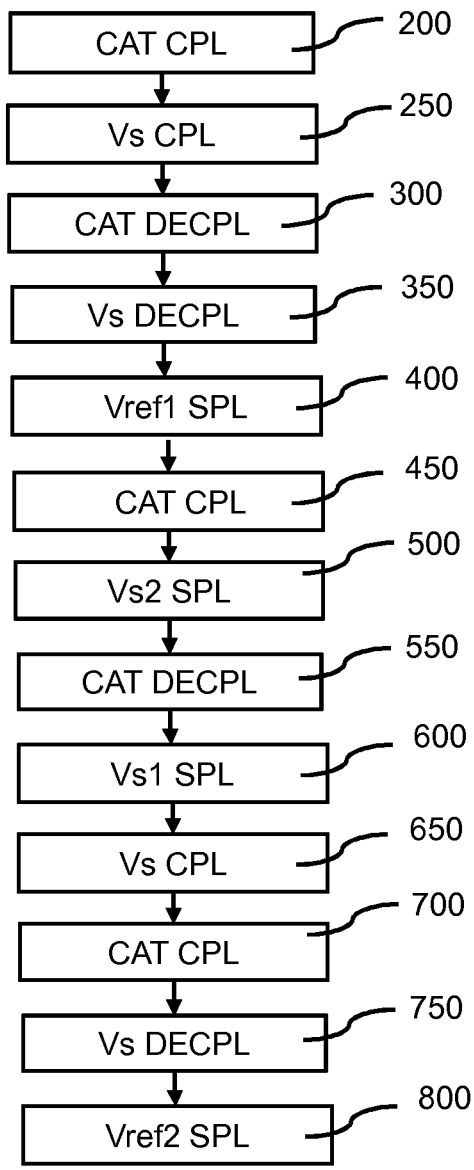
FIG. 3 shows a flow diagram for a method of controlling a pixel circuit.

FIG. 3 shows a flow diagram of a method of controlling a pixel circuit. The pixel circuit controlled may be of the type described in FIG. 1.

Figure 4:
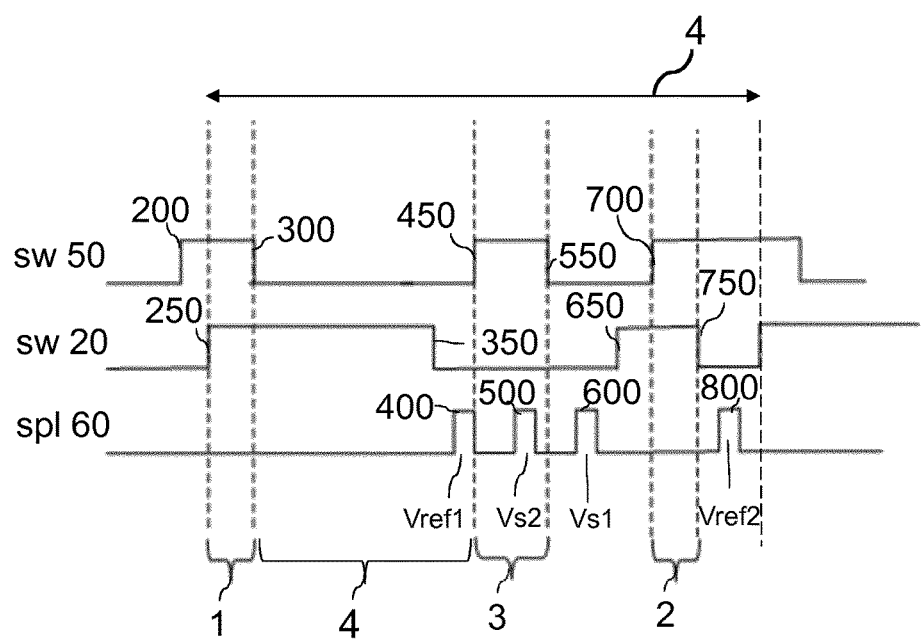
FIG. 4 shows a time diagram for the example shown in FIG. 1 and corresponding to the flow diagram as shown in FIG. 3.

FIG. 4 shows a time diagram for controlling the pixel circuit 100 described with reference to FIG. 1 and corresponding to the flow diagram as shown in FIG. 3.

Referring to the pixel circuit 100 of FIG. 1, the flow diagram of FIG. 3 and the time diagram of FIG. 4 the method comprises the following.

Electrically coupling 200, via the second switch 50, the cathode 42 to the first capacitor terminal 12 for at least a first reset time period 1.

Electrically coupling 250 a voltage source 30 to the first terminal 12 for at least the first reset time period 1. The voltage source 30 generates a voltage reference Vref.

After the first reset time period 1 has passed:
electrically decoupling 300, via the second switch 50, the cathode 42 from the voltage source 30 for accumulating the charge carriers in the photo diode for an accumulation time period 4.

During the accumulation time period 4:
electrically decoupling 350 the first capacitor terminal 12 from the voltage source 30,
sampling 400 a first reference voltage value Vref1 at the first capacitor terminal 12.

After the accumulation time period 4 has passed:
electrically coupling 450, via the second switch 50, the cathode 42 to the first capacitor terminal 12 for a selected transfer time period 3 for transferring the charge carriers to the first capacitor 10.

After the selected transfer time period 3 has passed:
electrically decoupling 550, via the second switch 50, the cathode 42 from the first capacitor terminal 12, and
sampling 600 a first signal voltage value Vs1.

The method further comprises:
sampling 500 a second signal voltage value Vs2 during the selected transfer time period 3.

After sampling 600 the first signal voltage value Vs1:
electrically coupling 650 the voltage source 30 to the first capacitor terminal 12 for at least a second reset time period 2,
electrically coupling 700, via the second switch 50, the cathode 42 to the first capacitor terminal 12 for a second reset time period 2.

After the second reset time period 2 has passed:
electrically decoupling 750 the voltage source 30 from the first capacitor terminal 12, and
sampling 800 a second reference voltage value Vref2 while the cathode 42 is electrically coupled via the second switch 50 to the first capacitor terminal 12.

It should be noted that waveforms shown in FIG. 4 are not drawn to scale.

Waveforms may be time periodic with time period 4. The time period 4 starts from the first reset time period 1 and ends after sampling 800 the second reference voltage value Vref2. Sampling 400 of the first reference voltage value Vref1, sampling 500 of the second signal voltage value Vs2, sampling 600 of the first signal voltage value Vs1 and sampling 800 of the second reference voltage value Vref2 are performed in a fixed sampling sequence. Said samplings 400, 500, 600 and 800 are performed after a single light exposure of the photo diode, i.e. after electrically decoupling 300 the cathode 42 from the voltage source 30 for accumulating the charge carriers in the photo diode. The second switch 50 has always an inherent transfer capacitance arranged in parallel to the first capacitor 10. When the cathode 42 is electrically coupled to the first capacitor terminal 12 via the second switch 50, the capacitance at the first capacitor terminal 12 is increased.

In FIG. 4 it is shown that the electrically coupling 200 starts before the electrically coupling 250. However, timing of the waveforms may be different, for example the electrically coupling 250 may start before or be simultaneous to the electrically coupling 200 as far as the cathode and the voltage source are electrically coupled to the first capacitor terminal 12 for a first reset time period 1.

Figure 5:
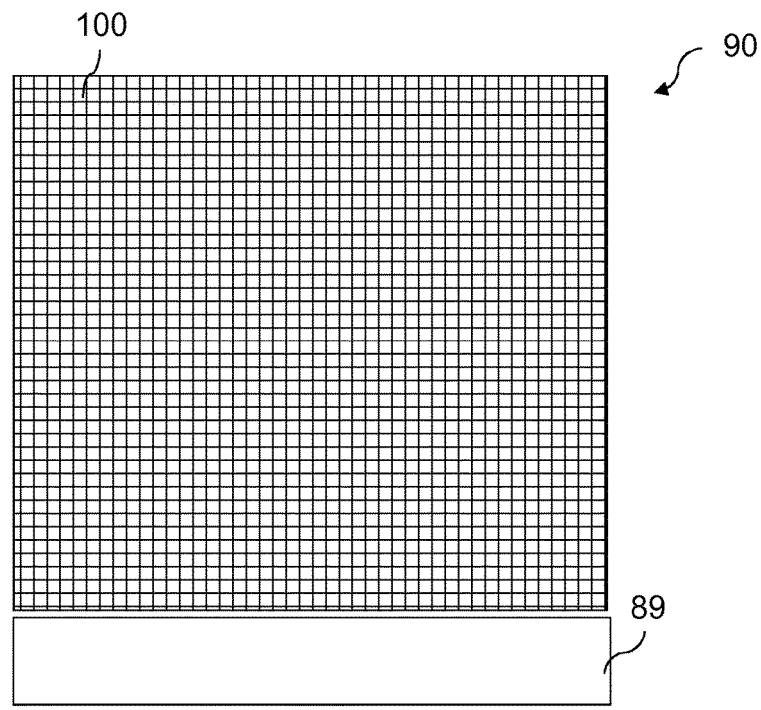
FIG. 5 shows an example of an image sensor.

FIG. 5 schematically shows a top view of an image sensor 90. The image sensor may comprise a plurality of pixel circuits arranged in array. The array may be structured in columns and rows in a matrix-like structure. Readout of an entire column or row may be e.g. activated by the third switch 68 as described with reference to FIG. 2. In the array the pixel circuits may be physically equivalent. The pixel circuit 100 as described with reference to FIG. 1 may be repeated throughout the array to form the image sensor 90. The image sensor 90 may include the parallel array 89 of at least four capacitors as shown in FIG. 1.

The image sensor 90 may be implemented in any manner specific for the specific implementation. For example, the image sensor 90 may also include the circuit controller 70 and/or the read out circuitry 88 and/or the reference voltage source 30. The image sensor 90 may be manufactured using a semiconductor technology of the group of semiconductor technologies comprising: a silicon, a silicon germanium, a gallium arsenide, a gallium nitride semiconductor technology, or a combination thereof. The image sensor may e.g. manufactured by using on one or more semiconductor wafers processed with any of the above mentioned semiconductor technologies. In case of large image sensors more semiconductor wafers may be attached together to form the image sensor 90.

The image sensor 90 may be used in any suitable application, e.g. in digital still cameras, security cameras, medical, automobiles, and other applications.

Figure 6:
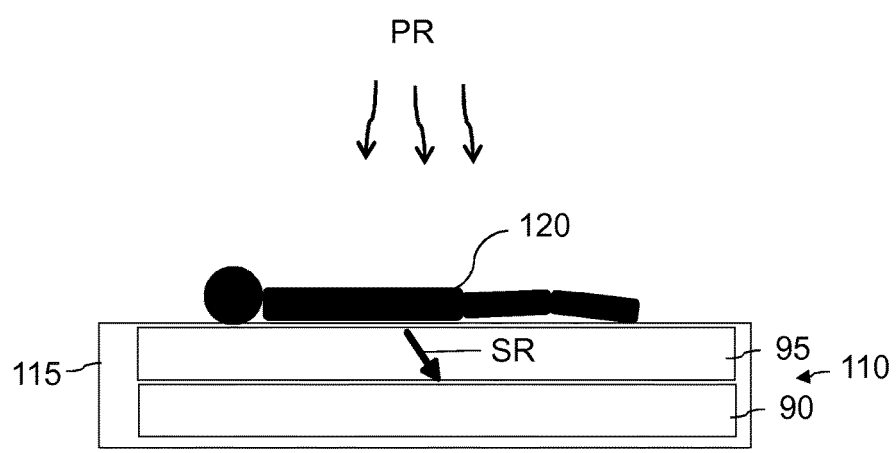
FIG. 6 shows an example of a radiation detector.

For example, FIG. 6 shows an example of a radiological instrument 115.

The radiological instrument comprises a radiation detector 110. The radiation detector 110 comprises the image sensor 90 as shown in FIG. 5 and a scintillator 95. The radiation detector 110 may be arranged to detect primary radiation PR for example through a body or a body part of a patient 120. The scintillator 95 may convert the primary radiation PR into secondary radiation SR. The scintillator 95 is coupled to the image sensor 90 such that the secondary radiation SR is transferred to the image sensor 90. The secondary radiation SR impinges on the image sensor 90, i.e. on the photo diodes of the image sensor 90. By processing the secondary radiation SR in the image sensor 90, an output image of the body or a body part of the patient 120 may be outputted. The output image may be a radiographic image that may be used to diagnose a condition of the patient 120.

The radiological instrument may be of any type suitable for the specific application: e.g. an intra-oral radiologic dental imager, a dental imager, a computed tomography scanner (CT-scanner), a computed axial tomography scanner (CAT-scanners), mobile C-arm, etc.

The radiation detector 110 may e.g. be a flat panel radiation detector. The radiation detector 110 may have a different shape than the flat shape shown in FIG. 6. The radiation detector 110 may have for example a non-flat surface, for example a concave or convex surface. The primary radiation PR may be X-ray radiation from an X-ray radiation source which penetrates the body of the patient 120 before impinging on the radiation detector 110.

The scintillator 95 may be a columnar or a non-columnar scintillator. For example the scintillator 95 may be a CsI:Tl (Caesium Iodide doped with thallium) scintillator or a Gadolinium oxysulfide scintillator layer, or otherwise.

The output image may be a planar image, a panoramic image or so-called tomographic image. Planar images are typically obtained by flat panel radiation detectors. Panoramic images may be obtained by a sequence of planar images taken one after another. Tomographic images may instead be obtained by a three-dimensional reconstruction of the specific areas of the body of the patient.

It should be noted that the above-mentioned embodiments illustrate rather than limit the invention, and that those skilled in the art will be able to design many alternative embodiments.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A circuit controller for controlling a pixel circuit, the pixel circuit (100) comprising:
   a first capacitor having a first capacitor terminal and a second capacitor terminal,
   a first switch for electrically coupling, when switched-on, the first capacitor terminal to a voltage source for generating a reference voltage (Vref),
   a photo diode for accumulating charge carriers upon exposure to incident light, the photo diode having a cathode and an anode, the anode being electrically coupled to the second capacitor terminal,
   a second switch for electrically coupling, when switched-on, the cathode to the first capacitor terminal,
   a sampling circuit having an input electrically coupled to the first capacitor terminal for sampling a voltage value at the first capacitor terminal,
   the circuit controller being configured for
   switching on the first switch and the second switch for a first reset time period,
   after the first reset time period, switching off the second switch for accumulating the charge carriers in the photo diode for an accumulation time period (4),
   during the accumulation time period,
      switching off the first switch, and
      controlling the sampling circuit to sample a first reference voltage value (Vref1),
   after the accumulation time period, switching on for a selected transfer time period the second switch for transferring the charge carriers to the first capacitor,
   after the selected transfer time period, switching off the second switch and controlling the sampling circuit to sample a first signal voltage value (Vs1), wherein
   the circuit controller is configured for
   controlling the sampling circuit to sample a second signal voltage value (Vs2) during the selected transfer time period,
   after sampling the first signal voltage value (Vs1), switching on the first switch and the second switch for a second reset time period,
   after the second reset time period, switching off the first switch, and
   controlling the sampling circuit to sample a second reference voltage value (Vref2) while the second switch is on.

2. The circuit controller of claim 1, further configured for controlling the sampling circuit for determining
   a first voltage difference by subtracting the first signal voltage value (Vs1) from the first reference voltage value (Vref1), and
   a second voltage difference by subtracting the second signal voltage value (Vs2) from the second reference signal voltage value (Vref2).

3. The circuit controller of claim 2, further configured for controlling the sampling circuit for selecting the first voltage difference as an output voltage of the pixel circuit when the first voltage difference is smaller than a predetermined voltage value and the second voltage difference when the first voltage difference is larger the predetermined voltage.

4. A pixel circuit comprising:
   a circuit controller comprising:
      a first capacitor having a first capacitor terminal and a second capacitor terminal (14),
      a first switch for electrically coupling, when switched-on, the first capacitor terminal to a voltage source for generating a reference voltage (Vref),
      a photo diode for accumulating charge carriers upon exposure to incident light, the photo diode having a cathode and an anode, the anode being electrically coupled to the second capacitor terminal,
      a second switch for electrically coupling, when switched-on, the cathode to the first capacitor terminal, a sampling circuit having an input electrically coupled to the first capacitor terminal for sampling a voltage value at the first capacitor terminal, the circuit controller being configured for switching on the first switch and the second switch for a first reset time period, after the first reset time period, switching off the second switch for accumulating the charge carriers in the photo diode for an accumulation time period, during the accumulation time period,
switching off the first switch, and
controlling the sampling circuit to sample a first reference voltage value (Vref1), after the accumulation time period, switching on for a selected transfer time period the second switch for transferring the charge carriers to the first capacitor, after the selected transfer time period, switching off the second switch and controlling the sampling circuit to sample a first signal voltage value (Vs1), wherein the circuit controller is configured for
controlling the sampling circuit to sample a second signal voltage value (Vs2) during the selected transfer time period, after sampling the first signal voltage value (Vs1), switching on the first switch and the second switch for a second reset time period, after the second reset time period, switching off the first switch, and controlling the sampling circuit to sample a second reference voltage value (Vref2) while the second switch is on, wherein the first switch has a first switch terminal electrically connected to the first capacitor terminal and a second switch terminal electrically coupled to the voltage source, and wherein the second switch has a third switch terminal electrically coupled to the cathode and a fourth switch terminal electrically connected to the first capacitor terminal.

5. The pixel circuit as claimed in claim 4, the sampling circuit comprising a buffer circuit and a third switch, the buffer circuit having an input electrically coupled to the first capacitor terminal and an output electrically connected to a an input terminal of the third switch, an output terminal of the third switch being electrically coupled to a parallel array of at least four capacitors for storing the first reference voltage value (Vref1), the first signal voltage value (Vs1), the second reference voltage value (Vref2) and the second signal voltage value (Vs2).

6. The pixel circuit as claimed in claim 5, the parallel array of at least four capacitors being electrically coupled to a readout circuitry for reading the first reference voltage value (Vref1), the second signal voltage value (Vs2), the first signal voltage value (Vs1) and the second reference voltage value (Vref2).

7. The pixel circuit as claimed in claim 4, the first switch, the second switch and the third switch comprising a transistor of the group of transistors consisting of: complementary metal oxide transistors, junction field effect transistors, metal effect semiconductor transistors, bipolar transistors, hetero junction bipolar transistors, insulated-gate bipolar junction transistors.

8. An image sensor comprising a plurality of pixels circuits arranged in an array, each pixel circuit comprising:
a circuit controller comprising:
a first capacitor having a first capacitor terminal and a second capacitor terminal (14), a first switch for electrically coupling, when switched-on, the first capacitor terminal to a voltage source for generating a reference voltage (Vref), a photo diode for accumulating charge carriers upon exposure to incident light, the photo diode having a cathode and an anode, the anode being electrically coupled to the second capacitor terminal, a second switch for electrically coupling, when switched-on, the cathode to the first capacitor terminal, a sampling circuit having an input electrically coupled to the first capacitor terminal for sampling a voltage value at the first capacitor terminal, the circuit controller being configured for switching on the first switch and the second switch for a first reset time period, after the first reset time period, switching off the second switch for accumulating the charge carriers in the photo diode for an accumulation time period, during the accumulation time period,
switching off the first switch, and
controlling the sampling circuit to sample a first reference voltage value (Vref1), after the accumulation time period, switching on for a selected transfer time period the second switch for transferring the charge carriers to the first capacitor, after the selected transfer time period, switching off the second switch and controlling the sampling circuit to sample a first signal voltage value (Vs1), wherein the circuit controller is configured for
controlling the sampling circuit to sample a second signal voltage value (Vs2) during the selected transfer time period, after sampling the first signal voltage value (Vs1), switching on the first switch and the second switch for a second reset time period, after the second reset time period, switching off the first switch, and controlling the sampling circuit to sample a second reference voltage value (Vref2) while the second switch is on, wherein the first switch has a first switch terminal electrically connected to the first capacitor terminal and a second switch terminal electrically coupled to the voltage source, and wherein the second switch has a third switch terminal electrically coupled to the cathode and a fourth switch terminal electrically connected to the first capacitor terminal.

9. The image sensor as claimed in claim 8, the image sensor being manufactured using a semiconductor technology of the group of semiconductor technologies comprising: a silicon, a silicon germanium, a gallium arsenide, a gallium nitride semiconductor technology, or a combination thereof.

10. A radiation detector for detecting primary radiation (PR) comprising the image sensor as claimed in claim 8, the radiation detector further comprising a scintillator for converting the primary radiation (PR) into secondary radiation (SR), the scintillator coupled to the image sensor for transferring the secondary radiation (SR) to the image sensor and outputting an image in response to the primary radiation (PR).

11. A method of controlling a pixel circuit, the pixel circuit comprising a first capacitor having a first capacitor terminal and a second capacitor terminal, a photo diode for accumulating charge carriers upon exposure to incident light, the photo diode having a cathode and an anode, the anode being electrically coupled to the second capacitor terminal, and a switch for electrically coupling, when switched-on, the cathode to the first capacitor terminal, the method comprising:
    electrically coupling via the switch the cathode to the first terminal for at least a first reset time period,
    electrically coupling a voltage source generating a voltage reference (Vref) to the first capacitor terminal for at least the first reset time period,
    after the first reset time period, electrically decoupling via the switch the cathode from the voltage source for accumulating the charge carriers in the photo diode for an accumulation time period;
    during the accumulation time period,
        electrically decoupling the first capacitor terminal from the voltage source,
        sampling a first reference voltage value (Vref1) at the first capacitor terminal,
    after the accumulation time period, electrically coupling, via the switch, the cathode to the first capacitor terminal for a selected transfer time period for transferring the charge carriers to the first capacitor,
    after the selected transfer time period,
        electrically decoupling via the switch the cathode from the first capacitor terminal,
        sampling a first signal voltage value (Vs1), wherein the method comprises:
        sampling a second signal voltage value (Vs2) during the selected transfer time period;
    after sampling the first signal voltage value (Vs1),
        electrically coupling the voltage source to the first capacitor terminal for at least a second reset time period,
        electrically coupling via the switch the cathode to the first capacitor terminal for at least the second reset time period;
    after the second reset time period,
        electrically decoupling the voltage source from the first capacitor terminal, and
        sampling a second reference voltage value (Vref2) while the cathode is electrically coupled via the switch to the first capacitor terminal.

* * * * *

UNITED STATES PATENT AND TRADEMARK OFFICE
CERTIFICATE OF CORRECTION

PATENT NO. : 10,154,211 B2
APPLICATION NO. : 15/513113
DATED : December 11, 2018
INVENTOR(S) : Willem Hendrik Maes It is certified that error appears in the above-identified patent and that said Letters Patent is hereby corrected as shown below:

In the Specification

Column 1, Line 17: Remove duplicate phrase "a pixel circuit"

Column 1, Line 55: Replace "while the signal voltage is still stored in the photo-diode" with --while the signal charges are still stored in the photo-diode--

Column 1, Line 61: Replace "A difference" with --The difference--

Column 7, Line 29: Replace "will further described" with --will further be described--

Signed and Sealed this
Ninth Day of April, 2019

Andrei Iancu
*Director of the United States Patent and Trademark Office*